United States Patent [19]

Giordano et al.

[11] Patent Number: 5,183,935

[45] Date of Patent: Feb. 2, 1993

[54] PROCESS FOR THE PREPARATION OF 5-(2',4'DIFLUOROPHENYL)-SALICYLIC ACID IN PURE FORM II

[75] Inventors: Claudio Giordano, Monza; Maurizio Paiocchi, Milan, both of Italy

[73] Assignee: Zambon Group S.p.A., Vicenza, Italy

[21] Appl. No.: 921,066

[22] Filed: Jul. 29, 1992

[30] Foreign Application Priority Data

Aug. 1, 1991 [IT] Italy .................... MI91A002152

[51] Int. Cl.$^5$ ............................................. C07C 69/76
[52] U.S. Cl. ..................................................... 562/469
[58] Field of Search ........................................ 562/469

[56] References Cited

U.S. PATENT DOCUMENTS

| | | | |
|---|---|---|---|
| 4,131,618 | 12/1978 | Weinstock et al. | 562/469 |
| 4,225,730 | 9/1980 | Jones et al. | 562/469 |
| 4,847,442 | 7/1989 | Nalelwajek | 570/142 |

FOREIGN PATENT DOCUMENTS

| | | |
|---|---|---|
| 0028407 | 5/1981 | European Pat. Off. . |
| 0101625 | 2/1984 | European Pat. Off. . |
| 254354 | 1/1988 | European Pat. Off. . |
| 367746 | 5/1990 | European Pat. Off. . |
| 3-223275 | 10/1991 | Japan . |
| 1175212 | 12/1969 | United Kingdom . |

OTHER PUBLICATIONS

Yin, M. et al. Yiyao Gongye, (9) 26–8 1984.
Shen T. Y. et al. INSERM Symp.; 23 (Platelet-Act. Factor Struct. Relat. Ether-Lipids 167–76 1983.
The Merck Index, XI ed., No., 3130. p. 495, 1989. Susan Budavari, ed. "2,4–Difluoroaniline."
Analytical Profiles of Drug Substances, pp. 491–526, 1985. Meredith L. Cotton and Robert A. Hux, "Diflunisal."
British Pharmacopoeia, pp. 191–192, 1988. "Diflunisal."

*Primary Examiner*—Paul J. Killos
*Attorney, Agent, or Firm*—Oblon, Spivak, McClelland, Maier & Neustadt

[57] ABSTRACT

A crystallization process of crude 5-(2',4'-difluorophenyl)-salicylic acid from a mixture of an aromatic hydrocarbon and an aliphatic ketone for preparing 5-(2',4'-difluorophenyl)-salicylic acid in form II substantially pure is described.

5 Claims, No Drawings

PROCESS FOR THE PREPARATION OF 5-(2',4'DIFLUOROPHENYL)-SALICYLIC ACID IN PURE FORM II

The present invention relates to a process for purifying 5-(2',4'-difluorophenyl)-salicylic acid and, more particularly, it relates to a crystallization process for the preparation of 5-(2',4'-difluorophenyl)-salicylic acid in a substantially pure crystalline form.

5-(2',4'difluorophenyl)-salicylic acid (Merck Index, XI ed., No. 3130, page 495), which will be hereinafter indicated as compound A, is a drug having anti-inflammatory activity known with the international non-proprietary name (INN) Diflunisal.

It is known that compound A is polymorphous since it exists in three crystalline forms commonly indicated as form I, form II and form III and that are distinguishable mainly on the base of the infrared absorption spectra [Analytical Profiles of Drug Substances—Meredith L. Cotton and Robert A. Hux—Diflunisal—pages 491-526, (1985)].

In particular, only form II satisfies the requisites required by the international Pharmacopoeia (British Pharmacopoeia 1988—pages 191-2 and USP XXII—pages 432-3).

From the literature some processes for the preparation of compound A are known, even if, as far as we know, only a few of these have industrial application.

British patent No. 1175212 (Merck & Co.) describes the preparation of compound A through a Gomberg reaction between a diazonium salt of 2,4-difluoroaniline and anisole, subsequent hydrolysis of the ether group and carboxylation.

U.S. Pat. No. 4,225,730 (Merck & Co.) reports the preparation of 2,4-difluoro-biphenyl, the Friedel-Crafts acylation with an acyl derivative of an aliphatic $C_2$-$C_5$ carboxylic acid, the oxidation of the 2,4-difluoro-biphenyl substituted in 4' with a $C_2$-$C_5$ alkylcarbonyl, thus obtained to give the corresponding 4'-alkylcarbonyloxy-2,4-difluoro-biphenyl, the hydrolysis to 4-(2,4-difluorophenyl)-phenol and its carboxylation to get compound A.

U.S. Pat. No. 4,131,618 (Merck & Co.) describes a process for the preparation of compound A by melting 2',4'-difluoro-4-acetoxy-1,1'-biphenyl with anhydrous sodium or potassium carbonate in the presence of $CO_2$ and at high pressure and temperature.

European patent No. 0028407 (Merck & Co.) reports the possibility of a "coupling" reaction between a salicylic ester and 1,3-difluorobenzene followed by hydrolysis of the ester to obtain compound A.

European patent No. 0101625 (Zambon S.p.A.) describes a process for the preparation of compound A by carboxylation of 4-(2,4-difluorophenyl)-phenol at atmospheric pressure with an alkali alkylcarbonate.

The purification of compound A obtained by the processes described in the above cited documents is carried out by crystallization from toluene or from benzene and methanol mixtures or isopropanol and water mixtures.

For simplicity hereinafter we will indicate as crude compound A both the compound A obtained directly by the preparation processes described in the above cited documents and the compound A obtained after purification according to said methods.

The crude compound A has a melting point generally comprised between 210° and 213° C.

However, in the literature the crystallographic purity of crude compound A or its other physical characteristics are not indicated.

We have verified that crude compound A is not crystallographically pure, namely it does not present an infrared absorption spectrum in accordance to the characteristics required by Pharmacopoeia.

In particular, from a crystallographic point of view, crude compound A resulted to consist of a mixture of polymorphous crystals (form I and form II) generally with prevalence of form I, i.e. of the unsuitable form.

We have now found an easy, unexpensive and simply industrially applicable method for crystallizing crude compound A thus obtaining the compound A in form II substantially pure, in accordance with the requisites of Pharmacopoeia, and furthermore with characteristics of bulk density and surface area particularly suitable for the preparation of pharmaceutical forms.

Therefore, object of the present invention is a process for the preparation of compound A in form II substantially pure, consisting in dissolving crude compound A in a mixture of solvents consisting of an aromatic hydrocarbon and an aliphatic ketone at the reflux temperature, in adding a seed of compound A in pure form II, in removing by distillation at least 90% by volume of the aliphatic ketone, in cooling to a temperature comprised between 10° and 20° C. and in filtering the suspension.

The precipitate collected by filtration is the desired compound A form II, crystallographically pure.

The process yields are particularly high, generally higher than 90%. Suitable aromatic hydrocarbons are, for example, benzene, toluene, o-xylene, m-xylene, p-xylene and mixtures thereof.

Suitable aliphatic ketones are, for example, acetone, methylethylketone, methylisobutylketone and mixtures thereof.

Preferably a mixture of toluene and acetone is employed.

The ratio between the solvents is not critical.

For practical reasons, it is preferred to dissolve compound A in a mixture containing about 20-30% by volume of aliphatic ketone, thus removing a portion of the ketone by distillation before the addition of the seed.

Even more preferred is the dissolution of crude compound A in a mixture of toluene and acetone having a reflux temperature comprised between 80° and 85° C.

The distillation has the purpose of removing the major portion of the ketone and is generally carried out at atmospheric pressure.

It clearly appears to the man skilled in the art that an analogous result can be obtained by working at reduced pressure and, consequently, at lower temperatures.

The cooling temperature is comprised between 10° and 20° C., preferably 15°-16° C.

The crystallization process, object of the present invention, allows to obtain compound A in form II substantially pure.

In particular the infrared absorption spectrum corresponds to that of reference (British Pharmacopoeia 1988, page 537—Diflunisal form A).

The mixture of solvents employed and the operative conditions used represent the most innovative aspect of the invention.

As far as we know, actually, none of the methods known in the literature for the preparation of compound A allows to obtain it in pure form II.

On this matter, it is significant the fact that by crystallization from toluene (see example 3) or from a mixture of benzene and methanol (see example 4) a mixture of polymorphic crystals is obtained, which is characterized by an infrared absorption spectrum not corresponding to the Pharmacopoeia.

A mixture of unsuitable polymorphic crystals is obtained also by crystallization from a mixture of isopropanol and water by adding a seed of compound A in pure form II (see example 5).

Particularly significant is the fact that even the normal crystallization from a mixture of toluene and acetone in a volumetric ratio of 9:1 does not allow to get compound A crystallographically pure (see example 6).

A practical embodiment of the process of the invention consists in the dissolution of the crude compound A in a mixture of toluene and acetone at a temperature of about 80°–85° C.

The solvent is distilled so as to remove a portion of acetone and a small amount of compound A in pure form II is seeded. The distillation of the solvent is continued up to an internal temperature of at least 100° C.

After cooling at 15°–16° C. over some hours, the suspension is filtered and the precipitate is washed and dried thus obtaining compound A in pure form II.

As already pointed out, the compound A obtained with the process of the invention is crystallographically pure since it satisfies the requisites of the Pharmacopoeia.

Furthermore, the compound A crystallographically pure obtained with the process of the invention is characterized by bulk density values comprised between 0.20 and 0.40 g/ml, by tamped apparent density values comprised between 0.30 and 0.50 g/ml and by a surface area comprised between 4.0 and 6.0 m$^2$/g.

It is important to point out that the characteristics of density and surface area of the compound A obtained according to the process of the invention are not achievable with any of the purification processes of the crude compound A described in the literature.

Therefore a further object of the present invention is compound A in form II substantially pure characterized by bulk density values comprised between 0.20 and 0.40 g/ml, by tamped apparent density values comprised between 0.30 and 0.50 g/ml and by a surface area comprised between 4.0 and 6.0 m$^2$/g.

The advantages of a product having the above mentioned characteristics of density and surface area are well-known to the man skilled in the art.

From the point of view of the pharmaceutical technology the increase of density causes mainly an improvement of the work-up of the product both in general and with particular reference to the productivity of the formulation process since it allows an increase of the loaded weight/occupied volume ratio.

The high surface area indeed is important, for a product scarcely soluble in water and free from hygroscopicity problems, since the absorption rate is improved.

This is of particular interest for the products having analgesic and anti-inflammatory activity, that are generally formulated in prompt-release pharmaceutical forms.

Further advantages of the process of the invention are the high yield, the high crystallographic purity of the product obtained, the cheapness and the easy industrial applicability.

Furthermore the process of the invention allows to obtain compound A in pure form starting from crude compound A, namely the compound A prepared according to one of the methods known in the literature, without requiring further purifications.

In order to better illustrate the present invention, the following examples are now given.

EXAMPLE 1

Crude 5-(2′,4′-difluorophenyl)-salicylic acid (250 g), prepared as described in U.S. Pat. No. 4,225,730, was dissolved in a mixture of toluene (1 l) and acetone (370 ml) at reflux temperature.

The solvent was distilled up to incipient crystallization.

The solution was seeded with 5-(2′,4′-difluorophenyl)-salicylic acid in pure form II (1.25 g).

The solvent (505 ml) was distilled up to an internal temperature of 102° C.

After cooling at 15° C. the suspension was filtered.

The precipitate was washed with toluene (150 ml) and methylene chloride (200 ml).

After drying under vacuum at 60° C. the product in pure form II (239 g—yield 95.6%) was obtained.

The product obtained had a bulk density of 0.37 g/ml and a tamped apparent density of 0.45 g/ml.

The surface area, determined with B.E.T. method was 4.48 m$^2$/g.

EXAMPLE 2

Crude 5-(2′,4′-difluorophenyl)-salicylic acid (25 g), prepared as described in European patent No. 0101625, was dissolved in a mixture of toluene (200 ml) and acetone (40 ml).

The solvent was distilled (66 ml) up to an internal temperature of 102°–103° C., and was seeded with 5-(2′,4′-difluorophenyl)-salicylic acid in pure form II (0.25 g).

After cooling at 15° C. the suspension was filtered.

The precipitate was washed with toluene (25 ml).

After drying under vacuum at 60° C. the product in pure form II (23.5 g—94% yield) was obtained.

EXAMPLE 3

Comparative Example—Crystallization from Toluene

A mixture of crude 5-(2′,4′-difluorophenyl)-salicylic acid (5.5 g), prepared as described in U.S. Pat. No. 4,225,730, in toluene (90 ml) was reflux heated.

The solution was cooled under stirring to 15° C. and kept at this temperature for 1 hour.

The precipitate was filtered and was washed with toluene (2×5 ml).

After drying under vacuum at 60° C. for 16 hours, 5-(2′,4′-difluorophenyl)-salicylic acid (5.3 g) was obtained having an infrared absorption spectrum not corresponding to that of reference (British Pharmacopoeia 1988, page 537—Diflunisal form A).

EXAMPLE 4

Comparative Example—Crystallization from a Mixture of Benzene and Methanol

A mixture of crude 5-(2′,4′-difluorophenyl)-salicylic acid (2.5 g), prepared as described in U.S. Pat. No. 4,225,730, in benzene (25 ml) and methanol (1.5 ml) was reflux heated.

The solution was cooled under stirring to 15° C.

The precipitate was filtered and washed with benzene (2×2 ml).

After drying under vacuum at 60° C., 5-(2′,4′-difluorophenyl)-salicylic acid (1.0 g) was obtained having an infrared absorption spectrum not corresponding to that of reference (British Pharmacopoeia 1988, page 537—Diflunisal form A).

EXAMPLE 5

Comparative Example—Crystallization from a Mixture of Isopropanol and Water

The procedure described in the example of U.S. Pat. No. 4,131,618 was repeated.

Sodium hydroxide (4 g) was added to a mixture of crude 5-(2',4'-difluorophenyl)-salicylic acid (12.5 g) in water (150 ml).

The mixture was heated to 95° C. and water (100 ml) and isopropanol (130 ml) were added.

Concentrated sulphuric acid (5 ml) was added dropwise to the solution, kept at 80° C.

The solution was cooled to 75° C. for 1 hour and a seed of 5-(2',4'-difluorophenyl)-salicylic acid (0.16 g) in pure form II was added. The suspension was kept at 75° C. for 1 hour and then was cooled in about four hours to 15° C.

The precipitate was filtered and washed with a mixture of water:isopropanol 2:1 (100 ml) and then with water (75 ml).

After drying under vacuum at 60° C. over 16 hours, 5-(2',4'-difluorophenyl)-salicylic acid (12.1 g) was obtained, having an infrared absorption spectrum not corresponding to that of reference (British Pharmacopoeia 1988, page 537—Diflunisal form A).

EXAMPLE 6

Comparative Example—Crystallization from a Mixture of Toluene and Acetone

A mixture of crude 5-(2',4'-difluorophenyl)-salicylic acid (6 g) in toluene (50 ml) and acetone (5 ml) was reflux heated.

The solution was cooled up to 20° C. under stirring for about 4 hours and kept at this temperature for one hour.

The precipitate was filtered and washed with toluene (2×5 ml).

After drying under vacuum at 60° C. for 16 hours, 5-(2',4'-difluorophenyl)-salicylic acid (3.7 g) was obtained having an infrared absorption spectrum not corresponding to that of reference (British Pharmacopoeia 1988, page 537—Diflunisal form A).

What we claim is:

1. A process for preparing 5-(2',4'-difluorophenyl)-salicylic acid in form II substantially pure, consisting in dissolving a mixture of polymorphous crystals of 5-(2',4'-fidluorophenyl)-salicylic acid in a mixture of solvents consisting of an aromatic hydrocarbon and an aliphatic ketone at the reflux temperature, in adding a seed of 5-(2',4'-difluorophenyl)-salicylic acid in pure form II, in removing by distillation at least 90% by volume of the aliphatic ketone, in cooling to a temperature comprised between 10° and 20° C. and in filtering the suspension.

2. A process according to claim 1 wherein the aromatic hydrocarbon is selected from the group consisting of benzene, toluene, o-xylene, m-xylene, p-xylene and mixtures thereof.

3. A process according to claim 1 wherein the aliphatic ketone is selected from the group consisting of acetone, methylethylketone, methylisobutylketone and mixtures thereof.

4. A process according to claim 1 wherein the aromatic hydrocarbon is toluene and the aliphatic ketone is acetone.

5. 5-(2',4'-difluorophenyl)-salicylic acid in form II substantially pure characterized by bulk density values comprised between 0.20 and 0.40 g/ml, tamped apparent density values comprised between 0.30 and 0.50 g/ml and a surface area comprised between 4.0 and 6.0 $m^2/g$.

* * * * *